(12) United States Patent
Kim et al.

(10) Patent No.: US 8,161,799 B1
(45) Date of Patent: Apr. 24, 2012

(54) APPARATUS AND METHODS FOR EVALUATION OF ENERGETIC MATERIALS

(75) Inventors: Steven S. Kim, Crofton, MD (US);
Harold W. Sandusky, Fulton, MD (US);
Carl Gotzmer, Acokeek, MD (US);
Kendall C. Elliott, Port Tobacco, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 684 days.

(21) Appl. No.: 12/287,165

(22) Filed: Sep. 30, 2008

(51) Int. Cl.
*G01N 33/22* (2006.01)
(52) U.S. Cl. ........................ 73/35.14; 73/35.17
(58) Field of Classification Search ............ 73/35.14, 73/35.17
See application file for complete search history.

(56) References Cited

U.S. PATENT DOCUMENTS

| | | | |
|---|---|---|---|
| 1,049,187 A * | 12/1912 | Olsen et al. | 73/35.14 |
| 1,801,449 A * | 4/1931 | Olsen et al. | 73/35.14 |
| 2,483,803 A * | 10/1949 | Bridgman et al. | 374/51 |
| 2,493,725 A * | 1/1950 | McMorris | 73/35.14 |
| 2,832,213 A * | 4/1958 | Cole, Jr. et al. | 73/35.17 |
| 3,545,252 A | 12/1970 | Springfield et al. | |
| 3,578,756 A | 5/1971 | Evans et al. | |
| 3,820,435 A | 6/1974 | Rogers et al. | |
| 4,990,312 A | 2/1991 | Rucker et al. | |
| 6,354,137 B1 | 3/2002 | Guirguis et al. | |
| 7,128,057 B2 | 10/2006 | Wiese et al. | |
| 7,159,448 B2 | 1/2007 | Moelkner et al. | |
| 7,669,460 B1 * | 3/2010 | Sandusky et al. | 73/35.16 |
| 2010/0039256 A1 * | 2/2010 | Manahan | 340/540 |

* cited by examiner

*Primary Examiner* — Freddie Kirkland, III
(74) *Attorney, Agent, or Firm* — Fredric J. Zimmerman

(57) ABSTRACT

The invention relates to an apparatus for evaluating energetic materials for ignitability, flamespread, pressure and thermal characteristics, energetic material interaction, and other properties. The invention is directed to an apparatus for analyzing the suitability of energetic materials for interactions with other energetic materials, explosive or non-explosive. The invention includes a vented combustion chamber, an ignition tube and a firing mechanism. The invention also includes methods for using the apparatus. For example, the apparatus of the invention may be used to analyze energetic materials for their use in destroying rubble which may contain explosive material.

18 Claims, 7 Drawing Sheets

APPARATUS AND METHODS FOR EVALUATION OF ENERGETIC MATERIALS

GOVERNMENT LICENSING CLAUSE

The invention described herein may be manufactured and used by or for the Government of the United States of America for governmental purposes without the payment of any royalties thereon or therefore.

FIELD OF THE INVENTION

The invention relates to novel apparatus and methods for evaluating energetic materials for ignitability, flamespread, pressure and thermal characteristics, energetic material interaction, and other properties. The invention also includes methods of using such an apparatus. The invention is particularly directed to an apparatus for analyzing the suitability of energetic materials for interactions with other energetic materials, explosive or non-explosive. For example, the apparatus of the invention may be used to analyze energetic materials for use in destroying rubble, which may itself contain explosive material.

BACKGROUND OF THE INVENTION

Whether energetic materials are to be employed as explosives, incendiaries, concussives, or other uses, they must be evaluated with regard to many properties to determine their suitable for such different uses. Such parameters may include ignitability, flamespread, pressure characteristics, thermal characteristics, energetic material interaction, and others. Traditional methods of examining energetic materials include large scale field tests and smaller scale analysis in test chambers.

For example, U.S. Pat. No. 3,545,252 describes a flammability test chamber which may be evacuated, filled with a desired gaseous environment for testing the test material, an ignition means, a probe for positioning of the test material, and a heating means. The chamber is essentially a crude explosion chamber, and it is incapable of the data collection achieved by the instant invention.

U.S. Pat. No. 3,578,756 describes an Autoignition Test Cell similar to that of U.S. Pat. No. 3,545,252. U.S. Pat. No. 4,990,312 describes a high-pressure promoted combustion chamber having a plurality of viewing ports. U.S. Pat. No. 6,354,137 describes a testing chamber for small amounts of explosive. U.S. Pat. No. 7,159,448 describes a pressure-determining combustion chamber, comprising a sensor having a piezoresistive thin metallic layer. U.S. Pat. No. 3,820,435 describes a system said to be useful for high-explosive studies, and "readily allows flash radiography of an event as it occurs. U.S. Pat. No. 7,128,057 describes a device for determining fuel quality.

While these test chambers may provide certain useful data, they are not readily adaptable to providing data regarding a plurality of properties (e.g., temperature, pressure, flammability, etc.) all in a single test. Moreover, they are not readily adaptable to the investigation of an energetic material's interaction with other energetic materials. In contrast, as indicated below, the inventive apparatus may be used to evaluate any single energetic material reaction or interactions between several energetic materials. Applications include evaluation of ignition behavior of an ignition energetic material against another material. The apparatus includes a method to control rupture pressure to evaluate the energetic material response to different rupture pressures.

The destruction of explosive mine rubble is a dangerous endeavor. Typically, energetic material is employed for such destruction, however, determining suitable compositions to be used for this purpose has essentially required full scale testing in the field in order to ascertain the particular characteristics of the composition, its effectiveness in destroying rubble, the attendant environment of the destruction process, and other parameters. Full scale field testing is prohibitively expensive, is capable of testing only a single composition per field test, and bears the risk of destroying the very instruments employed to collect data for the evaluation of the material.

The testing chambers in the art are unable to provide the necessary analysis because they do not provide results for multiple parameters and they are not suitable for interaction analysis.

The art is in need of improved tools for analyzing energetic materials.

SUMMARY OF THE INVENTION

Accordingly, it an object of the present invention to provide an apparatus capable of analyzing multiple parameters of an energetic material, including ignition, thermal, and pressure characteristics. The apparatus of the invention is also able to provide data regarding the interaction of energetic materials with other energetic materials, be they explosive or non-explosive. Additionally, the apparatus may be used with relatively small amounts of energetic material, and provide a more cost-effective means of evaluating energetic materials as well as permit tests to be repeated without the added cost of preparing full scale field tests in the early evaluation phase. Further, many such materials may be evaluated more quickly.

In an exemplary embodiment of the invention, the apparatus includes a combustion chamber, an ignition tube, and a firing mechanism. The apparatus is provided with instrument ports for the collection of a variety of data, including temperature, pressure, and heat flux measurements.

Other objects and advantages of the present invention are evident from the entirety of this specification and the drawings.

In one aspect, the invention is directed to an apparatus for evaluating energetic materials which includes a vented combustion chamber including a counterbore and a plurality of instrument ports for attachment of a plurality of instruments, an ignition tube inserted within the counterbore, the ignition tube including an ignition material, a first energetic material, and a burst disk, and a firing mechanism.

The instruments may be selected from among detectors for temperature, pressure, and heat flux, and other instruments. The combustion chamber may also have a burst port, and a burst seal affixed thereto. The burst seal, as well as the burst disk attached to the initiation tube, are adapted to burst at a desired pressure.

In another aspect, the combustion chamber may also have a cavity containing a second energetic material, thereby providing the ability to analyze the interaction of the two energetic materials. The invention is particular advantageous when the second energetic material is explosive mine rubble.

In another aspect of the invention, the firing mechanism includes a piston and a firing pin. In order to operate the apparatus and collect data results, an initiation means may be used, and may be selected from the group consisting of electrical, pressure, and impact means. Upon activation of the initiation means, a cascade of events occurs, the events including firing of the firing mechanism, ignition of the ignition material, ignition of the first energetic material, and injection of the ignited energetic material into an interior of the combustion chamber. Data is collected from the plurality of instruments.

In another aspect, the combustion chamber also includes a translucent window for optical observation, allowing visual observation and high speed video recording. Also, a combustion containment basin may be used to collect reactant products after an operation of the apparatus.

In another aspect, the invention provides a method of evaluating a first energetic material by analyzing data collected from the plurality of instruments connected to any apparatus of the invention, as well as visual data and examination of the containment basin contents.

These and other features of the invention are exemplified and further described in the Detailed Description of the Invention below.

DETAILED DESCRIPTION OF THE INVENTION

Figure 1A:
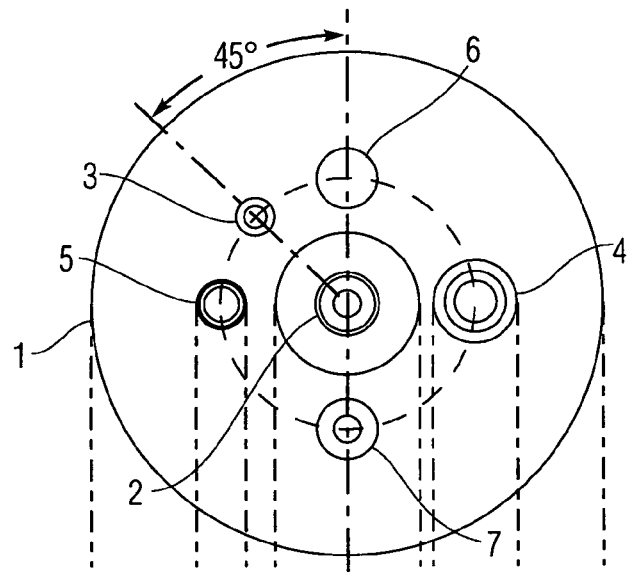
FIG. 1 is a schematic view of the combustion chamber according to an exemplary embodiment of the invention.

The present invention provides an apparatus capable of analyzing multiple properties of an energetic material, including ignition, thermal, and pressure characteristics, as well as information regarding interaction of the energetic material with other energetic materials. Energetic materials include explosives, incendiaries, concussive materials, and the like. Exemplary examples of energetic compositions are explosive compositions, such as, RDX and TNT explosives; flammable solids, such as, Thermite; oxidizers, such as, lithium perchlorate; and reactive materials, such as, nanoscale aluminum.

The advantages of the invention are achieved by providing multiple instrument access ports in the combustion chamber, into which a variety of instruments capable of providing different property measurements are affixed. The ability to investigate the interaction of energetic materials is provided by a cavity in the combustion chamber such that upon ignition of the first energetic material and its injection into the combustion chamber, the energetic materials interact and the instruments provide data to the investigator. A general description of the apparatus of the invention follows, after which exemplary embodiments of the invention will be more particularly described in the Examples.

In one embodiment of the invention, the apparatus of the invention includes a vented combustion chamber, an ignition tube, a firing mechanism, and a capture basin. The combustion chamber is constructed from steel or other materials capable of withstanding the pressure caused by combustion without significant deformation. The combustion chamber may be designed to accommodate different volumes, depending on the need of the investigator, the nature of the energetic material being analyzed, and the nature of the second energetic material whose interaction with the first energetic material is being analyzed. The vented combustion chamber is optionally provided with a burst port adapted for insertion of a burst seal designed to burst at a specified pressure. This burst port is independent of the ignition burst disk. The chamber burst port controls the chamber burst pressure to evaluate the effect of chamber pressure confinement on energetic material reaction rate. Materials generally react faster with higher pressure confinement. The chamber burst port may also serve as a pressure release port for safety purposes. The burst seal may be constructed from a variety of materials, such as metal shims, in order to achieve the desired burst pressure. Alternatively, where no burst seal is required, the burst port may be closed.

The combusion chamber is provided with instrumentation ports allowing for the collection of measurements of relevant properties, such as pressure, temperature, and heat flux. The combustion chamber is also provided on an outer surface with a counterbore passing completely therethrough, the counterbore having a narrower portion at the combustion chamber's interior surface, such that an ignition tube may be inserted in the counterbore, and prevented from entering the interior of the combustion chamber. The outer surface of the burst disk is thereby open to the interior of the combustion chamber.

The combustion chamber is provided with a cavity which may be left empty to evaluate an energetic material by itself, or which may be filled with a second energetic material to evaluate the reaction between the two materials.

The ignition tube contains the energetic material being analyzed. Generally, the maximum amount of material in the ignition tube depends on the size and strength of the combustion chamber and ignition tube. For a small ignition tube and chamber, the amount of material may be less than a gram. For a larger ignition tube and chamber, which is structurally stronger, perhaps several hundreds of grams may be tested. The ignition tube is hollowed at one end, thereby providing an ignition cup for holding the energetic material. The ignition cup end of the ignition tube is sealed with a burst disk. The burst disk is selected from suitable materials for retaining the ignited energetic material until the reaction pressure in the ignition tube builds up to a desired pressure, at which pressure the burst disk bursts and the ignited energetic material reactants are injected into the chamber cavity.

Generally, if the chamber does not involve the burst port and rupture window, then the chamber may survive and, depending upon the chamber size, hold greater than 100 PSI peak pressure. The burst disk that is on the ignition tube may be as low as about several hundred psi to about several thousand psi depending upon the material. Temperature does not affect the burst disk but it directly affects the reaction of the material itself. The opposite end of the ignition tube is also hollowed, and contains the ignition material to be ignited by a firing mechanism. The ignition material and the energetic material may be separated by a thin separating material, such as a mylar disk.

The firing machanism is secured to the top of the combustion chamber, such that its lower end abuts the ignition material end of the ignition tube. The firing mechanism may be used to initiate a variety of ignition sources, for example, electrical, pressure, or impact initiation.

In operation, the firing mechanism is activated, which initates the ignition material in the ignition tube, the energy of which is then transferred to the energetic material loaded in the ignition cup portion of the ignition tube. The energetic material is thereby ignited, building pressure until the pressure has reached the burst point for the ignition cup burst disk. The burst disk bursts, and the ignited reactants are injected into the chamber cavity.

The combustion chamber may be provided with an optical window to allow for visual observation and high speed video photography of the ignition event and flame spread. The optical window may be made from any translucent inert material sufficiently strong and of sufficient thickness to withstand the pressure in the combustion chamber.

In embodiments of the invention in which the interaction of the energetic material with a second energetic material is being analyzed, the second energetic material is situated in the chamber cavity, and a combustion containment basin is positioned below the chamber to capture the reaction products. The basin may further contain a liner to facilitate debris collection and may be used as a visible indicator of the completeness of the combustion.

EXAMPLES

The present invention will be further understood by reference to the following non-limiting examples.

(Actual) Example 1

An Apparatus of the Invention

Figure 1B:
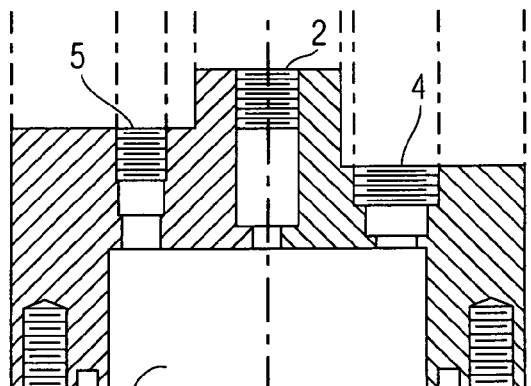
Figure 1C:
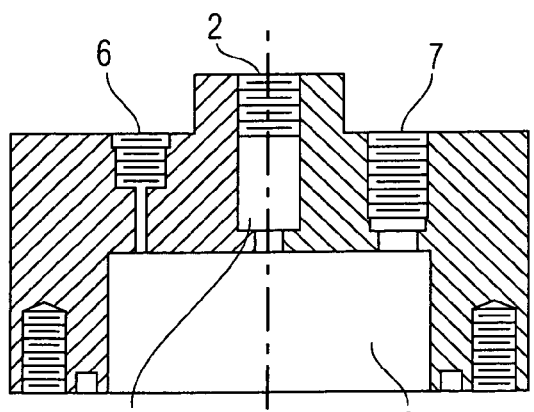

With reference to the FIG. 1, an apparatus of the invention was constructed with a steel combustion chamber (1) having a counterbore (2) on its upper surface. The combustion chamber (1) was 3 inches in diameter, and 2 inches in height. The upper surface also was provided with instrument ports: a thermocouple port (3), a heat flux port (4), and a pressure transducer port (5). The upper surface further comprises a vent connection (6), and a burst seal mounting (7). The counterbore, ports, vent, and burst seal mounting each abut the combustion chamber interior (8).

Figure 2A:
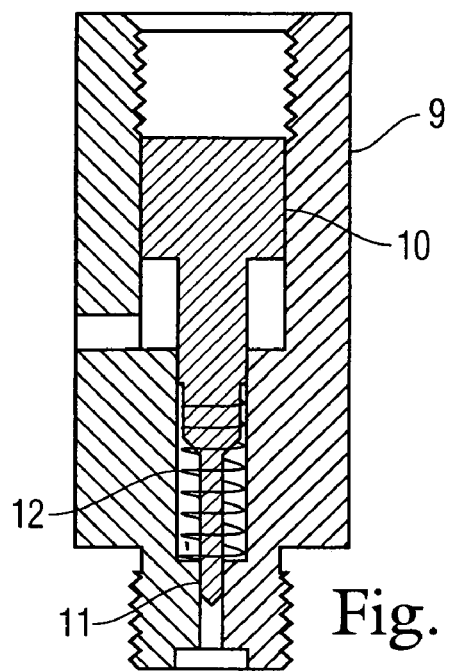
FIG. 2 is a schematic view of the primer firing mechanism and ignition cup according to an embodiment of the invention.
Figure 2B:
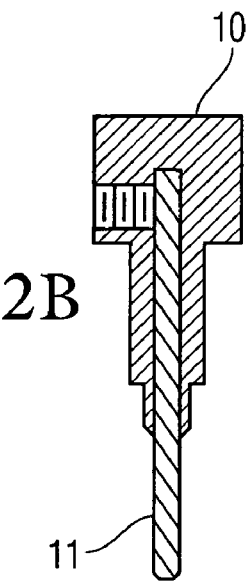
Figure 2C:
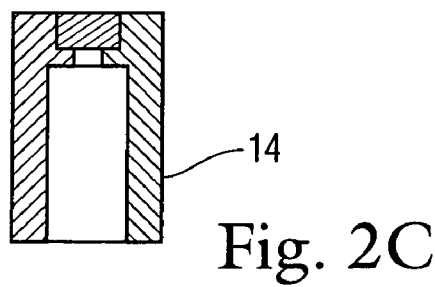
Figure 3:
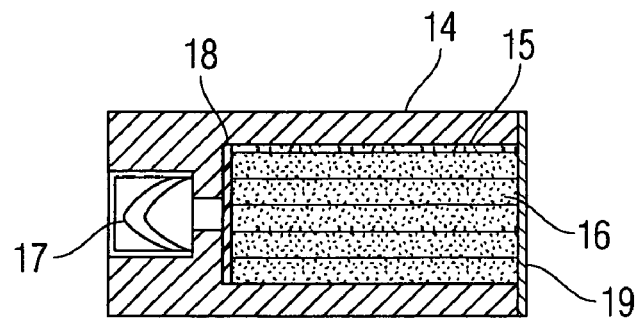
FIG. 3 is a detailed view of an ignition cup according to an embodiment of the invention.

With reference to FIGS. 2 and 3, a steel firing mechanism (9) comprises a steel piston (10) and steel pin (11), shown in the retracted pre-firing position supported by a coil spring (12). The lower portion of the firing mechanism (9) is threaded to securely fasten into the counterbore's (2) matching threads. The counterbore's (2) lower un-threaded portion (13) is sized to accommodate the steel ignition tube (14), which has an ignition cup (15) containing energetic material (16) and ignition material (17) separated by a mylar disc (18), and a steel burst disk (19) glued to the end of the ignition tube with cyanoacrylate.

In FIGS. 2 and 3, the brass disk (19) was adhered to the bottom of the igniter cup (ignition tube) (15). In an exemplary embodiment, the disk (19) is a brass disk. The disk may be any material that matches the desired burst pressure.

Figure 4:
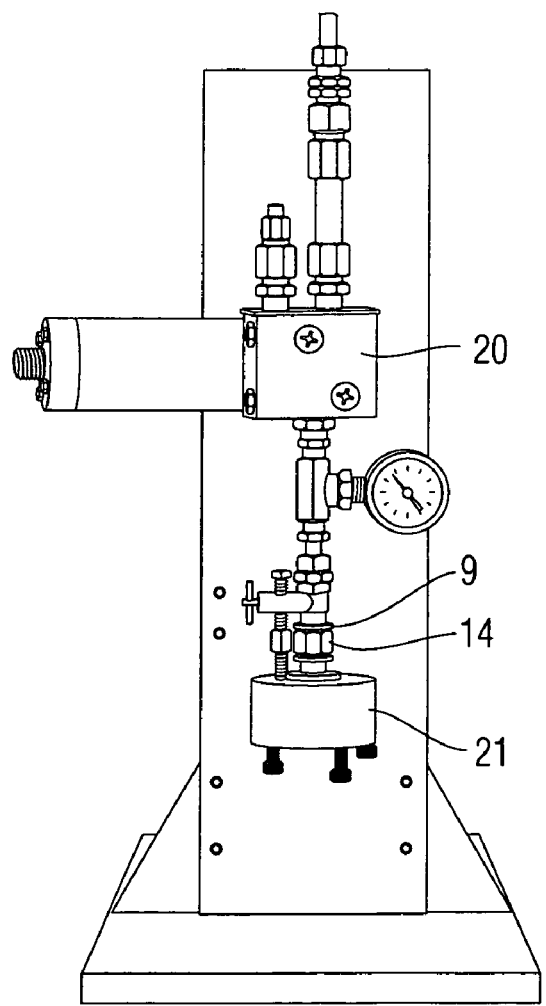
FIG. 4 is a photograph according to an embodiment of the invention.

As depicted in FIG. 4, the combustion chamber (1) is loaded with the ignition tube (14) and the firing mechanism (9). Attached to the top of the firing mechanism is a system to provide pressure to initiate the firing. Additionally, a pressure switch (20) and a plastic window are provided (21).

Figure 5:
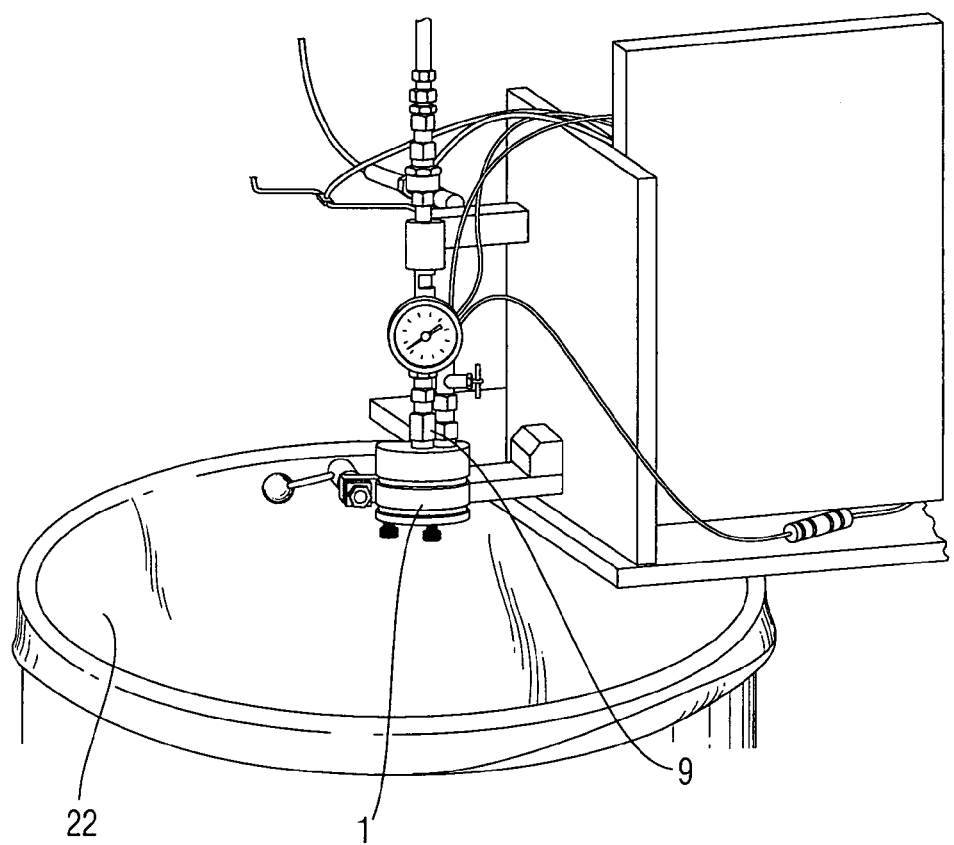
FIG. 5 is a photograph of an apparatus according to an embodiment of the invention.

As depicted in FIG. 5, a combustion containment basin (22) is provided, having a heat resistant liner, to collect the debris from the reaction for further examination. The debris generally falls into the catch basin (22). The vent on a bottom of the chamber is a rupture disk that may break away at the pressure desired. Note, the rupture disk may be changed to a disk made of a thick steel, which does not rupture.

Example 2

Operation of an Apparatus of the Invention

In operation, the pressure system is activated, which in turn initiates the firing mechanism, which ignites the ignition material, which ignites the energetic material, which bursts the burst disk. The ignited reactants enter the interior of the chamber. The instruments attached through the instrument ports collect data during the operation. Where a second energetic material, such as explosive mine rubble, is present in a cavity of the combustion chamber (not shown), the incoming ignited reactants interact with the second energetic material, thereby providing additional information to the investigator.

The apparatus as described in Example 1 was operated more than 120 times to analyze a variety of energetic materials. Metal/oxidizer reactive materials and explosives, that is, TNT, were tested using an M42 primer as the ignition material. Thirty-two operations of the apparatus included TNT rubble as a second energetic material, placed in the cavity of the combustion chamber. The amount of rubble tested was 37 grams of explosive rubble. Generally, the amount is greater based on a size of the chamber. Data was collected for the properties of temperature, pressure, and heat flux. Visible combustion products were collected in the combustion containment basin, and examined to determine relative levels of combustion for the various energetic materials. The results provided a successful screening of energetic materials for those which had superior performance in combustion of TNT rubble, i.e., ignitability, high thermal output, low pressure, and improved mine rubble consumption.

Four operations of the apparatus, the energetic material GSI Baseline OXMIET (S/N A23) "M" rated produced only partial combustion of the second energetic material, TNT rubble, with 18.1 grams remaining. NJIT ZnNaNO3 (S/N ZN4) "H" rated fared better, leaving 5.9 grams of black residue, while GSI Hafnium OXIMET (S/N A37) "H" rated left 3.5 grams of residue. By contrast, DET TFE/HFP Terpolymer (S/N 3NM-5) "L" rated left 26.5 grams unconsumed, including TNT pellets.

Figure 6:
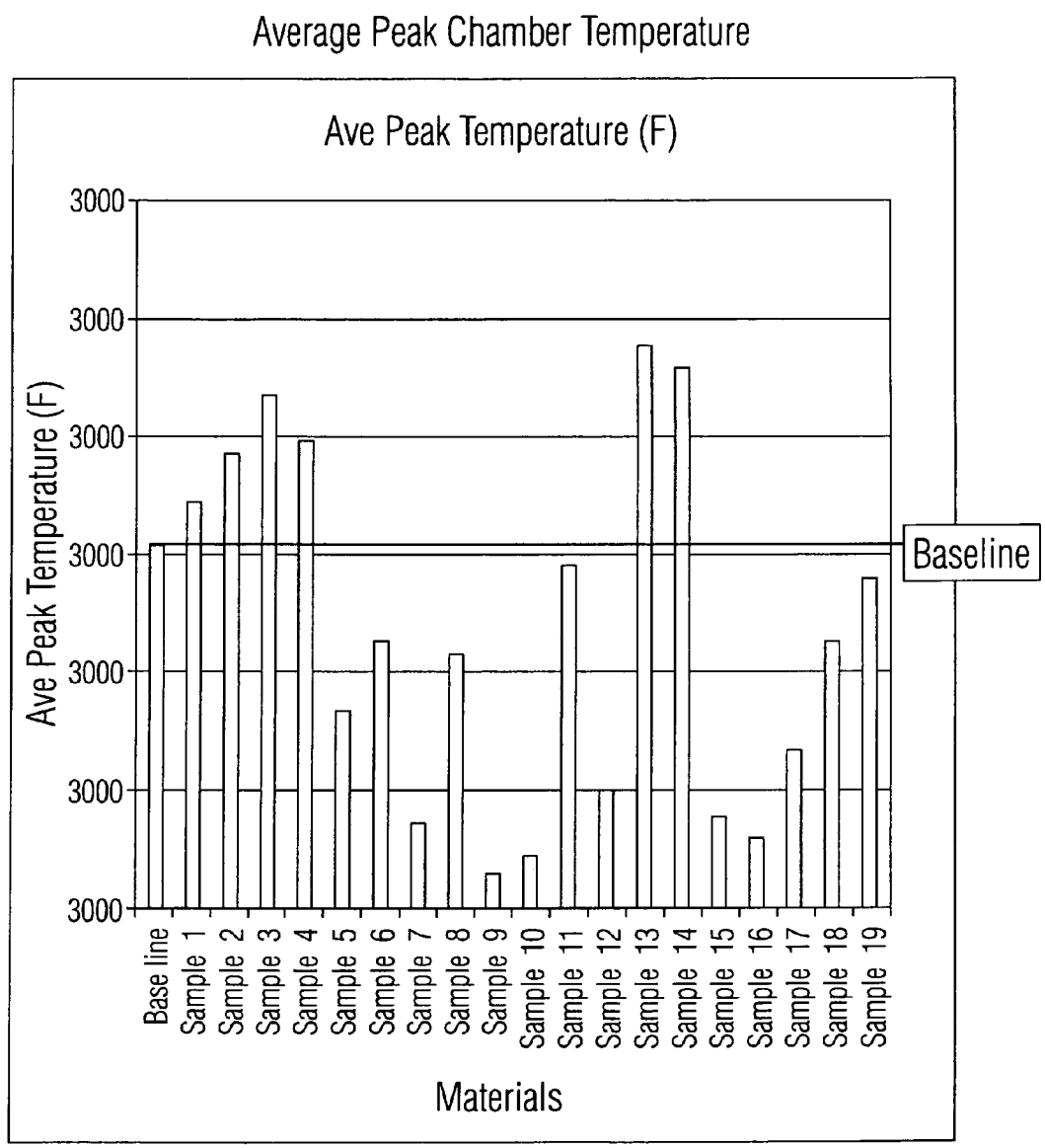
FIG. 6 is a graph of data pertaining to average peak chamber temperature versus the type of material.
Figure 7:
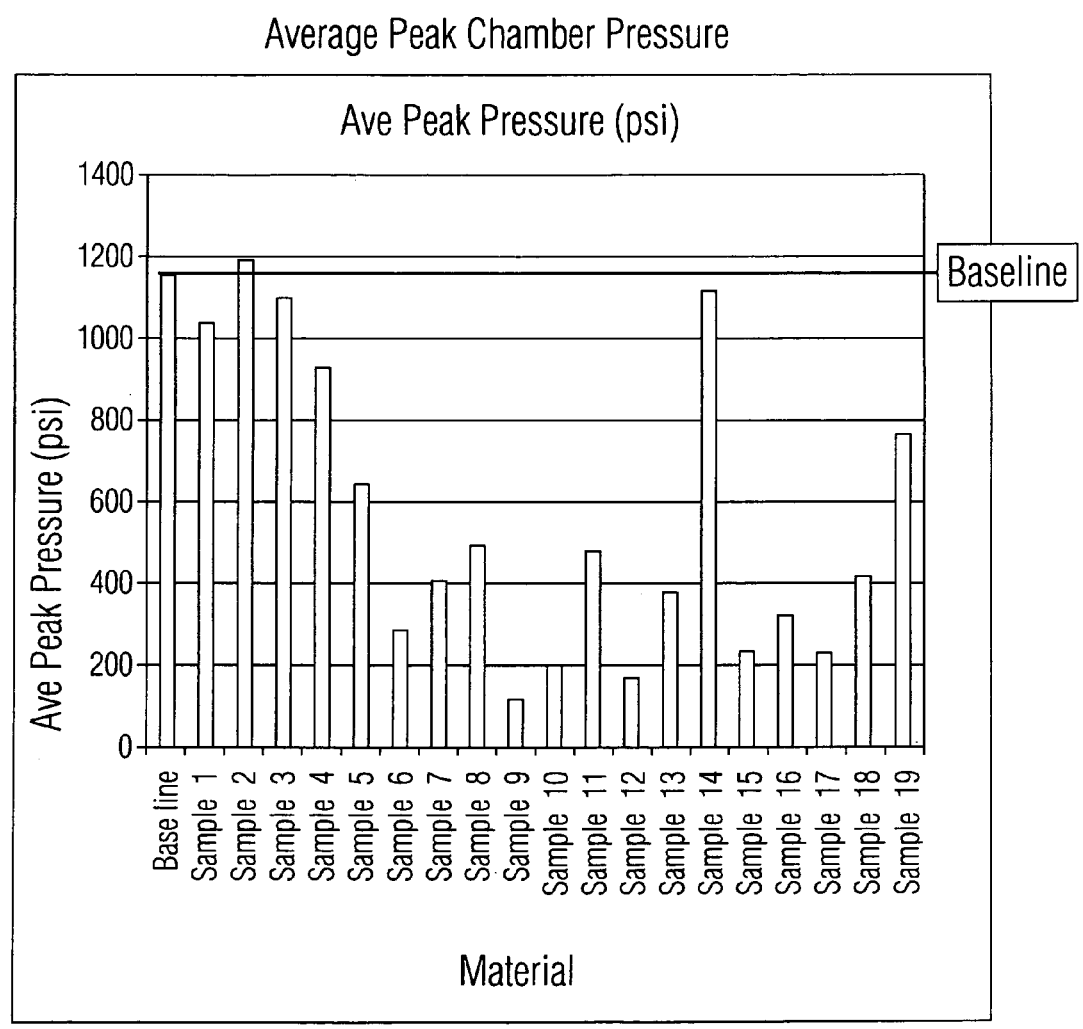
FIG. 7 is a graph of data pertaining to average peak chamber pressure versus the type of material.
Figure 8:
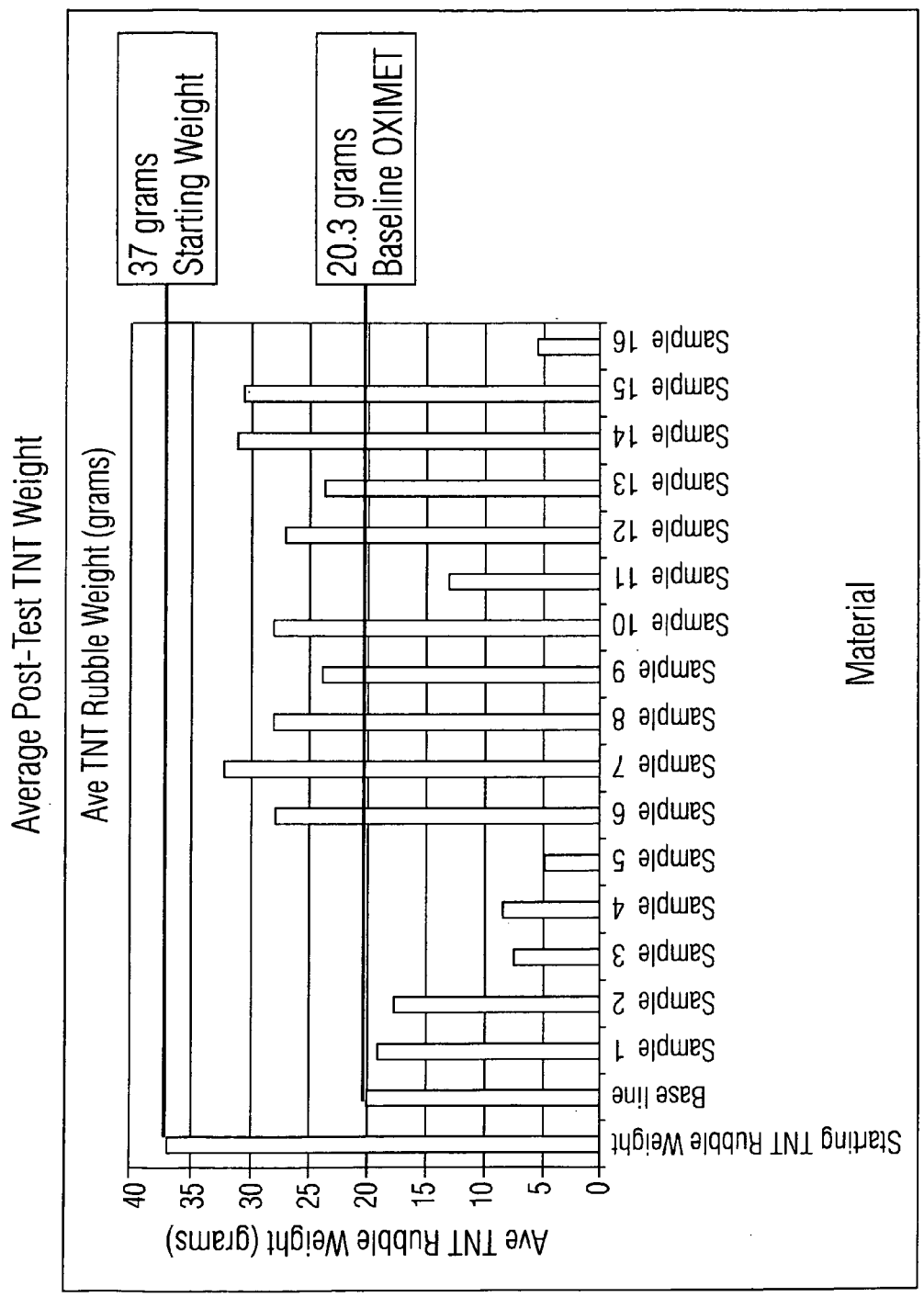
FIG. 8 is a graph of data pertaining to average post-test TNT weight versus the type of material.

Based on the apparatus and operation of the invention as indicated above, FIGS. 6, 7 and 8 provide graphs of actual test data. FIG. 6 provides data pertaining to average peak chamber temperature versus the type of material. FIG. 7 provides data pertaining to average peak chamber pressure versus the type of material. FIG. 8 provides data pertaining to average post-test TNT weight versus the type of material.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

We claim:

1. An apparatus for evaluating energetic materials, comprising:
    a combustion chamber comprising a counterbore and a plurality of instrument ports for attaching a plurality of instruments;
    an ignition tube being inserted within the counterbore, the ignition tube comprises an ignition material, a first energetic material, and a burst disk; and
    a firing mechanism being threaded into the counterbore, wherein the combustion chamber is a vented combustion chamber, and wherein the combustion chamber further comprises a cavity, which includes a second energetic material.

2. The apparatus of claim 1, wherein the plurality of instruments are at least two selected from the group consisting of detectors for temperature, pressure, and heat flux.

3. The apparatus of claim 1, wherein the combustion chamber further comprises a burst port, and wherein a burst seal is affixed to the burst port.

4. The apparatus of claim 1, wherein the second energetic material is explosive mine rubble.

5. The apparatus of claim 1, wherein the firing mechanism comprises a piston and a firing pin.

6. The apparatus of claim 1, further comprising an initiation structure.

7. The apparatus of claim 6, wherein the initiation structure is selected from the group consisting of electrical, pressure, and impact means.

8. The apparatus of claim 6, wherein the plurality of instruments generate data for collection subsequent to activation of the initiation structure.

9. The apparatus of claim 1, wherein the combustion chamber further comprises a translucent window for optical observation.

10. The apparatus of claim 9, wherein the translucent window is accessible for high speed video photography.

11. The apparatus of claim 1, wherein the burst disk is adapted to burst at a desired pressure.

12. The apparatus of claim 11, wherein the burst disk is a steel burst disk.

13. The apparatus of claim 1, further comprising a combustion containment basin.

14. A method of evaluating a first energetic material, comprising:

analyzing data being collected from a plurality of instruments being connected to an apparatus, wherein the apparatus comprises a combustion chamber comprises a counterbore and a plurality of instrument ports for attachment of the plurality of instruments, wherein the apparatus comprises an ignition tube inserted within the counterbore where the ignition tube comprises an ignition material, a first energetic material, and a burst disk, wherein the apparatus comprises a firing mechanism, and an initiation structure, and wherein the apparatus further comprises a cavity, which contains a second energetic material.

15. The method of claim 14, wherein the second energetic material is explosive mine rubble.

16. The method of claim 14, wherein the apparatus further comprises a translucent window.

17. The method of claim 16, wherein the data collected comprises high speed video taken through the translucent window.

18. The method of claim 14, wherein upon activation of the initiation structure, a cascade of events occurs, the events include firing of the firing mechanism, ignition of the ignition material, ignition of the first energetic material, and injection of ignited reactants into an interior of the combustion chamber.

* * * * *